United States Patent
Sartor

(10) Patent No.: US 9,532,826 B2
(45) Date of Patent: Jan. 3, 2017

(54) SYSTEM AND METHOD FOR SINUS SURGERY

(71) Applicant: COVIDIEN LP, Mansfield, MA (US)

(72) Inventor: Joe D. Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 254 days.

(21) Appl. No.: 14/159,758

(22) Filed: Jan. 21, 2014

(65) Prior Publication Data

US 2014/0257276 A1 Sep. 11, 2014

Related U.S. Application Data

(60) Provisional application No. 61/773,609, filed on Mar. 6, 2013.

(51) Int. Cl.
*A61B 18/04* (2006.01)
*A61B 17/00* (2006.01)
*A61B 18/00* (2006.01)

(52) U.S. Cl.
CPC .... *A61B 18/042* (2013.01); *A61B 2017/00323* (2013.01); *A61B 2018/00327* (2013.01)

(58) Field of Classification Search
CPC ............... A61B 2018/00327; A61B 2018/122; A61B 2018/00583; A61B 18/042; A61B 18/1485
USPC .............................. 606/41, 46; 607/105, 135
See application file for complete search history.

(56) References Cited

U.S. PATENT DOCUMENTS

| | | | |
|---|---|---|---|
| 438,257 A | 10/1890 | Raquet | |
| 2,213,820 A | 9/1940 | Maxson | |
| 2,598,301 A | 5/1952 | Rajchman | |
| 3,134,947 A | 5/1964 | Charasz | |
| 3,434,476 A | 3/1969 | Shaw et al. | |
| 3,492,074 A | 1/1970 | Rendina | |
| 3,671,195 A | 6/1972 | Bersin | |
| 3,687,832 A | 8/1972 | Fydelor et al. | |

(Continued)

FOREIGN PATENT DOCUMENTS

| CN | 2391565 Y | 8/2000 |
|---|---|---|
| DE | 3710489 A1 | 11/1987 |

(Continued)

OTHER PUBLICATIONS

European Serach Report corresponding to European Application No. 09 84 5328, dated Dec. 11, 2014; 8 pages.

(Continued)

*Primary Examiner* — Michael Peffley
*Assistant Examiner* — Thomas Giuliani

(57) ABSTRACT

A method for treating a sinus cavity is provided. The method includes the steps of inserting a plasma applicator into a sinus cavity defined in a bone mass, positioning the plasma applicator adjacent a tissue formation, generating a selectively reactive plasma effluent at the plasma applicator and directing the selectively reactive plasma effluent at the tissue formation. The selective nature of the reactive plasma enables treatment of specific targets inside the sinus while minimizing the effect on other tissues. Such treatment includes, but not limited to, sterilization of bacterial colonies, vaporization of unwanted tissues or foreign masses, stimulation of tissues by enriching the content of reactive oxygen and nitrous oxide pathways, and combinations thereof.

9 Claims, 4 Drawing Sheets

(56) References Cited

U.S. PATENT DOCUMENTS

| | | |
|---|---|---|
| 3,838,242 A | 9/1974 | Goucher |
| 3,903,891 A | 9/1975 | Brayshaw |
| 3,938,525 A | 2/1976 | Coucher |
| 3,991,764 A | 11/1976 | Incropera et al. |
| 4,010,400 A | 3/1977 | Hollister |
| 4,017,707 A | 4/1977 | Brown et al. |
| 4,143,337 A | 3/1979 | Beaulieu |
| 4,177,422 A | 12/1979 | Deficis et al. |
| 4,181,897 A | 1/1980 | Miller |
| 4,188,426 A | 2/1980 | Auerbach |
| 4,274,919 A | 6/1981 | Jensen et al. |
| 4,337,415 A | 6/1982 | Durr |
| 4,517,495 A | 5/1985 | Piepmeier |
| 4,577,165 A | 3/1986 | Uehara et al. |
| 4,629,887 A | 12/1986 | Bernier |
| 4,629,940 A | 12/1986 | Gagne et al. |
| 4,665,906 A | 5/1987 | Jervis |
| 4,699,082 A | 10/1987 | Hakim |
| 4,780,803 A | 10/1988 | Garcia-Santamaria |
| 4,781,175 A | 11/1988 | McGreevy et al. |
| 4,818,916 A | 4/1989 | Morrisroe |
| 4,837,484 A | 6/1989 | Eliasson et al. |
| 4,855,563 A | 8/1989 | Beresnev et al. |
| 4,877,999 A | 10/1989 | Knapp et al. |
| 4,901,719 A | 2/1990 | Trenconsky et al. |
| 4,922,210 A | 5/1990 | Flachenecker et al. |
| 4,956,582 A | 9/1990 | Bourassa |
| 5,013,959 A | 5/1991 | Kogelschatz |
| 5,025,373 A | 6/1991 | Keyser, Jr. et al. |
| 5,041,110 A | 8/1991 | Fleenor |
| 5,067,957 A | 11/1991 | Jervis |
| 5,088,997 A | 2/1992 | Delahuerga et al. |
| 5,098,430 A | 3/1992 | Fleenor |
| 5,117,088 A | 5/1992 | Stava |
| 5,120,703 A | 6/1992 | Snyder et al. |
| 5,124,526 A | 6/1992 | Muller et al. |
| 5,135,604 A | 8/1992 | Kumar et al. |
| 5,155,547 A | 10/1992 | Casper et al. |
| 5,157,015 A | 10/1992 | Snyder et al. |
| 5,159,173 A | 10/1992 | Frind et al. |
| 5,180,949 A | 1/1993 | Durr |
| 5,194,740 A | 3/1993 | Kogelschatz et al. |
| 5,217,457 A | 6/1993 | Delahuerga et al. |
| 5,223,457 A | 6/1993 | Mintz et al. |
| 5,256,138 A | 10/1993 | Burek et al. |
| 5,280,154 A | 1/1994 | Cuomo et al. |
| 5,300,068 A | 4/1994 | Rosar et al. |
| 5,304,279 A | 4/1994 | Coultas et al. |
| 5,320,621 A | 6/1994 | Gordon et al. |
| 5,334,834 A | 8/1994 | Ito et al. |
| RE34,780 E | 11/1994 | Trenconsky et al. |
| 5,383,019 A | 1/1995 | Farrell et al. |
| 5,384,167 A | 1/1995 | Nishiwaki et al. |
| 5,401,350 A | 3/1995 | Patrick et al. |
| 5,404,219 A | 4/1995 | D'Silva |
| 5,449,356 A | 9/1995 | Walbrink et al. |
| 5,449,432 A | 9/1995 | Hanawa |
| 5,466,424 A | 11/1995 | Kusano et al. |
| 5,505,729 A | 4/1996 | Rau |
| 5,526,138 A | 6/1996 | Sato |
| 5,534,231 A | 7/1996 | Savas |
| 5,554,172 A | 9/1996 | Horner et al. |
| 5,607,509 A | 3/1997 | Schumacher et al. |
| 5,618,382 A | 4/1997 | Mintz et al. |
| 5,656,186 A | 8/1997 | Mourou et al. |
| 5,669,904 A | 9/1997 | Platt, Jr. et al. |
| 5,669,907 A | 9/1997 | Platt, Jr. et al. |
| 5,683,366 A | 11/1997 | Eggers et al. |
| 5,688,357 A | 11/1997 | Hanawa |
| 5,697,882 A | 12/1997 | Eggers et al. |
| 5,707,402 A | 1/1998 | Heim |
| 5,708,330 A | 1/1998 | Rothenbuhler et al. |
| 5,720,745 A | 2/1998 | Farin et al. |
| 5,733,511 A | 3/1998 | De Francesco |
| 5,776,255 A | 7/1998 | Asaba et al. |
| 5,780,862 A | 7/1998 | Siess |
| 5,810,764 A | 9/1998 | Eggers et al. |
| 5,818,581 A | 10/1998 | Kurosawa et al. |
| 5,841,531 A | 11/1998 | Gliddon |
| 5,843,019 A | 12/1998 | Eggers et al. |
| 5,843,079 A | 12/1998 | Suslov |
| 5,845,488 A | 12/1998 | Hancock et al. |
| 5,849,136 A | 12/1998 | Mintz et al. |
| 5,858,477 A | 1/1999 | Veerasamy et al. |
| 5,865,937 A | 2/1999 | Shan et al. |
| 5,866,871 A | 2/1999 | Birx |
| 5,866,985 A | 2/1999 | Coultas et al. |
| 5,869,832 A | 2/1999 | Wang et al. |
| 5,892,328 A | 4/1999 | Shang et al. |
| 5,908,441 A | 6/1999 | Bare |
| 5,909,086 A | 6/1999 | Kim et al. |
| 5,945,790 A | 8/1999 | Schaefer |
| 5,961,772 A | 10/1999 | Selwyn |
| 5,977,715 A | 11/1999 | Li et al. |
| 6,013,075 A | 1/2000 | Avramenko et al. |
| 6,020,794 A | 2/2000 | Wilbur |
| 6,024,733 A | 2/2000 | Eggers et al. |
| 6,027,601 A | 2/2000 | Hanawa |
| 6,030,667 A | 2/2000 | Nakagawa et al. |
| 6,033,582 A | 3/2000 | Lee et al. |
| 6,036,878 A | 3/2000 | Collins |
| 6,046,546 A | 4/2000 | Porter et al. |
| 6,047,700 A | 4/2000 | Eggers et al. |
| 6,053,172 A | 4/2000 | Hovda et al. |
| 6,063,079 A | 5/2000 | Hovda et al. |
| 6,063,084 A | 5/2000 | Farin |
| 6,063,937 A | 5/2000 | Dlubala et al. |
| 6,066,134 A | 5/2000 | Eggers et al. |
| 6,074,386 A | 6/2000 | Goble et al. |
| 6,086,585 A | 7/2000 | Hovda et al. |
| 6,099,523 A | 8/2000 | Kim et al. |
| 6,102,046 A | 8/2000 | Weinstein et al. |
| 6,105,581 A | 8/2000 | Eggers et al. |
| 6,109,268 A | 8/2000 | Thapliyal et al. |
| 6,110,395 A | 8/2000 | Gibson, Jr. |
| 6,113,597 A | 9/2000 | Eggers et al. |
| 6,132,575 A | 10/2000 | Pandumsoporn et al. |
| 6,137,237 A | 10/2000 | MacLennan et al. |
| 6,142,992 A | 11/2000 | Cheng et al. |
| 6,149,620 A | 11/2000 | Baker et al. |
| 6,153,852 A | 11/2000 | Blutke et al. |
| 6,159,208 A | 12/2000 | Hovda et al. |
| 6,159,531 A | 12/2000 | Dang et al. |
| 6,170,428 B1 | 1/2001 | Redeker et al. |
| 6,172,130 B1 | 1/2001 | Bellesort |
| 6,172,324 B1 | 1/2001 | Birx |
| 6,178,918 B1 | 1/2001 | van Os et al. |
| 6,179,836 B1 | 1/2001 | Eggers et al. |
| 6,182,469 B1 | 2/2001 | Campbell et al. |
| 6,183,655 B1 | 2/2001 | Wang et al. |
| 6,190,381 B1 | 2/2001 | Olsen et al. |
| 6,197,026 B1 | 3/2001 | Farin et al. |
| 6,203,542 B1 | 3/2001 | Ellsberry et al. |
| 6,206,871 B1 | 3/2001 | Zanon et al. |
| 6,206,878 B1 | 3/2001 | Bishop et al. |
| 6,207,924 B1 | 3/2001 | Trassy |
| 6,210,402 B1 | 4/2001 | Olsen et al. |
| 6,210,410 B1 | 4/2001 | Farin et al. |
| 6,213,999 B1 | 4/2001 | Platt, Jr. et al. |
| 6,221,094 B1 | 4/2001 | Bare |
| 6,222,186 B1 | 4/2001 | Li et al. |
| 6,224,592 B1 | 5/2001 | Eggers et al. |
| 6,225,593 B1 | 5/2001 | Howieson et al. |
| 6,228,078 B1 | 5/2001 | Eggers et al. |
| 6,228,082 B1 | 5/2001 | Baker et al. |
| 6,228,229 B1 | 5/2001 | Raaijmakers et al. |
| 6,235,020 B1 | 5/2001 | Cheng et al. |
| 6,237,526 B1 | 5/2001 | Brcka |
| 6,238,391 B1 | 5/2001 | Olsen et al. |
| 6,242,735 B1 | 6/2001 | Li et al. |
| 6,248,250 B1 | 6/2001 | Hanawa et al. |
| 6,252,354 B1 | 6/2001 | Collins et al. |
| 6,254,600 B1 | 7/2001 | Willink et al. |
| 6,254,738 B1 | 7/2001 | Stimson et al. |

(56) References Cited

U.S. PATENT DOCUMENTS

| | | |
|---|---|---|
| 6,264,650 B1 | 7/2001 | Hovda et al. |
| 6,264,651 B1 | 7/2001 | Underwood et al. |
| 6,264,652 B1 | 7/2001 | Eggers et al. |
| 6,270,687 B1 | 8/2001 | Ye et al. |
| 6,277,112 B1 | 8/2001 | Underwood et al. |
| 6,277,251 B1 | 8/2001 | Hwang et al. |
| 6,283,961 B1 | 9/2001 | Underwood et al. |
| 6,287,980 B1 | 9/2001 | Hanazaki et al. |
| 6,291,938 B1 | 9/2001 | Jewett et al. |
| 6,296,636 B1 | 10/2001 | Cheng et al. |
| 6,296,638 B1 | 10/2001 | Davison et al. |
| 6,299,948 B1 | 10/2001 | Gherardi et al. |
| 6,309,387 B1 | 10/2001 | Eggers et al. |
| 6,313,587 B1 | 11/2001 | MacLennan et al. |
| 6,326,584 B1 | 12/2001 | Jewett et al. |
| 6,326,739 B1 | 12/2001 | MacLennan et al. |
| 6,328,760 B1 | 12/2001 | James |
| 6,329,757 B1 | 12/2001 | Morrisroe et al. |
| 6,333,481 B2 | 12/2001 | Augeraud et al. |
| 6,345,588 B1 | 2/2002 | Stimson |
| 6,346,108 B1 | 2/2002 | Fischer |
| 6,348,051 B1 | 2/2002 | Farin et al. |
| 6,353,206 B1 | 3/2002 | Roderick |
| 6,355,032 B1 | 3/2002 | Hovda et al. |
| 6,363,937 B1 | 4/2002 | Hovda et al. |
| 6,365,063 B2 | 4/2002 | Collins et al. |
| 6,375,750 B1 | 4/2002 | van Os et al. |
| 6,376,972 B1 | 4/2002 | Tarasenko et al. |
| 6,379,351 B1 | 4/2002 | Thapliyal et al. |
| 6,387,088 B1 | 5/2002 | Shattuck et al. |
| 6,391,025 B1 | 5/2002 | Weinstein et al. |
| 6,396,214 B1 | 5/2002 | Grosse et al. |
| 6,401,652 B1 | 6/2002 | Mohn et al. |
| 6,407,513 B1 | 6/2002 | Vollkommer et al. |
| 6,409,933 B1 | 6/2002 | Holland et al. |
| RE37,780 E | 7/2002 | Lanzani et al. |
| 6,416,507 B1 | 7/2002 | Eggers et al. |
| 6,416,508 B1 | 7/2002 | Eggers et al. |
| 6,416,633 B1 | 7/2002 | Spence |
| 6,424,099 B1 | 7/2002 | Kirkpatrick et al. |
| 6,424,232 B1 | 7/2002 | Mavretic et al. |
| 6,432,103 B1 | 8/2002 | Ellsberry et al. |
| 6,432,260 B1 | 8/2002 | Mahoney et al. |
| 6,443,948 B1 | 9/2002 | Suslov |
| 6,444,084 B1 | 9/2002 | Collins |
| 6,445,141 B1 | 9/2002 | Kastner et al. |
| 6,459,066 B1 | 10/2002 | Khater et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,464,889 B1 | 10/2002 | Lee et al. |
| 6,464,891 B1 | 10/2002 | Druz et al. |
| 6,468,270 B1 | 10/2002 | Hovda et al. |
| 6,468,274 B1 | 10/2002 | Alleyne et al. |
| 6,471,822 B1 | 10/2002 | Yin et al. |
| 6,474,258 B2 | 11/2002 | Brcka |
| 6,475,217 B1 | 11/2002 | Platt |
| 6,482,201 B1 | 11/2002 | Olsen et al. |
| 6,488,825 B1 | 12/2002 | Hilliard |
| 6,497,826 B2 | 12/2002 | Li et al. |
| 6,500,173 B2 | 12/2002 | Underwood et al. |
| 6,501,079 B1 | 12/2002 | Furuya |
| 6,502,416 B2 | 1/2003 | Kawasumi et al. |
| 6,502,588 B2 | 1/2003 | Li et al. |
| 6,507,155 B1 | 1/2003 | Barnes et al. |
| 6,525,481 B1 | 2/2003 | Klima et al. |
| 6,534,133 B1 | 3/2003 | Kaloyeros et al. |
| 6,540,741 B1 | 4/2003 | Underwood et al. |
| 6,544,261 B2 | 4/2003 | Ellsberry et al. |
| 6,558,383 B2 | 5/2003 | Cunningham et al. |
| 6,565,558 B1 | 5/2003 | Lindenmeier et al. |
| 6,575,968 B1 | 6/2003 | Eggers et al. |
| 6,579,289 B2 | 6/2003 | Schnitzler |
| 6,579,426 B1 | 6/2003 | van Gogh et al. |
| 6,582,423 B1 | 6/2003 | Thapliyal et al. |
| 6,582,427 B1 | 6/2003 | Goble et al. |
| 6,582,429 B2 | 6/2003 | Krishnan et al. |
| 6,589,237 B2 | 7/2003 | Woloszko et al. |
| 6,589,437 B1 | 7/2003 | Collins |
| 6,595,990 B1 | 7/2003 | Weinstein et al. |
| 6,617,794 B2 | 9/2003 | Barnes et al. |
| 6,624,583 B1 | 9/2003 | Coll et al. |
| 6,625,555 B2 | 9/2003 | Kuan et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,642,526 B2 | 11/2003 | Hartley |
| 6,646,386 B1 | 11/2003 | Sirkis et al. |
| 6,652,717 B1 | 11/2003 | Hong |
| 6,653,594 B2 | 11/2003 | Nakamura et al. |
| 6,657,594 B2 | 12/2003 | Anderson |
| 6,659,106 B1 | 12/2003 | Hovda et al. |
| 6,663,017 B2 | 12/2003 | Endres et al. |
| 6,666,865 B2 | 12/2003 | Platt |
| 6,685,803 B2 | 2/2004 | Lazarovich et al. |
| 6,712,811 B2 | 3/2004 | Underwood et al. |
| 6,719,754 B2 | 4/2004 | Underwood et al. |
| 6,719,883 B2 | 4/2004 | Stimson |
| 6,723,091 B2 | 4/2004 | Goble et al. |
| 6,726,684 B1 | 4/2004 | Woloszko et al. |
| 6,740,842 B2 | 5/2004 | Johnson et al. |
| 6,746,447 B2 | 6/2004 | Davison et al. |
| 6,763,836 B2 | 7/2004 | Tasto et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,774,569 B2 | 8/2004 | de Vries et al. |
| 6,780,178 B2 | 8/2004 | Palanker et al. |
| 6,780,184 B2 | 8/2004 | Tanrisever |
| 6,781,317 B1 | 8/2004 | Goodman |
| 6,787,730 B2 | 9/2004 | Coccio et al. |
| 6,805,130 B2 | 10/2004 | Tasto et al. |
| 6,806,438 B2 | 10/2004 | Nakano et al. |
| 6,815,633 B1 | 11/2004 | Chen et al. |
| 6,818,140 B2 | 11/2004 | Ding |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,840,937 B2 | 1/2005 | Van Wyk |
| 6,849,191 B2 | 2/2005 | Ono et al. |
| 6,852,112 B2 | 2/2005 | Platt |
| 6,855,143 B2 | 2/2005 | Davison et al. |
| 6,855,225 B1 | 2/2005 | Su et al. |
| 6,861,377 B1 | 3/2005 | Hirai et al. |
| 6,867,859 B1 | 3/2005 | Powell |
| 6,876,155 B2 | 4/2005 | Howald et al. |
| 6,890,332 B2 | 5/2005 | Truckai et al. |
| 6,896,672 B1 | 5/2005 | Eggers et al. |
| 6,896,674 B1 | 5/2005 | Woloszko et al. |
| 6,896,775 B2 | 5/2005 | Chistyakov |
| 6,909,237 B1 | 6/2005 | Park et al. |
| 6,911,029 B2 | 6/2005 | Platt |
| 6,915,806 B2 | 7/2005 | Pacek et al. |
| 6,919,527 B2 | 7/2005 | Boulos et al. |
| 6,920,883 B2 | 7/2005 | Bessette et al. |
| 6,921,398 B2 | 7/2005 | Carmel et al. |
| 6,922,093 B2 | 7/2005 | Kanda |
| 6,924,455 B1 | 8/2005 | Chen et al. |
| 6,929,640 B1 | 8/2005 | Underwood et al. |
| 6,949,096 B2 | 9/2005 | Davison et al. |
| 6,949,887 B2 | 9/2005 | Kirkpatrick et al. |
| 6,958,063 B1 | 10/2005 | Soll et al. |
| 6,974,453 B2 | 12/2005 | Woloszko et al. |
| 6,991,631 B2 | 1/2006 | Woloszko et al. |
| 7,004,941 B2 | 2/2006 | Tvinnereim et al. |
| 7,019,253 B2 | 3/2006 | Johnson et al. |
| 7,046,088 B2 | 5/2006 | Ziegler |
| 7,048,733 B2 | 5/2006 | Hartley et al. |
| 7,070,596 B1 | 7/2006 | Woloszko et al. |
| 7,084,832 B2 | 8/2006 | Pribyl |
| 7,090,672 B2 | 8/2006 | Underwood et al. |
| 7,096,819 B2 | 8/2006 | Chen et al. |
| 7,100,532 B2 | 9/2006 | Pribyl |

(56) References Cited

U.S. PATENT DOCUMENTS

| | | |
|---|---|---|
| 7,104,986 B2 | 9/2006 | Hovda et al. |
| 7,115,185 B1 | 10/2006 | Gonzalez et al. |
| 7,122,035 B2 | 10/2006 | Canady |
| 7,122,965 B2 | 10/2006 | Goodman |
| 7,131,969 B1 | 11/2006 | Hovda et al. |
| 7,132,620 B2 | 11/2006 | Coelho et al. |
| 7,132,996 B2 | 11/2006 | Evans et al. |
| 7,150,745 B2 | 12/2006 | Stern et al. |
| 7,157,857 B2 | 1/2007 | Brouk et al. |
| 7,160,521 B2 | 1/2007 | Porshnev et al. |
| 7,161,112 B2 | 1/2007 | Smith et al. |
| 7,164,484 B2 | 1/2007 | Takahashi et al. |
| 7,165,451 B1 | 1/2007 | Brooks et al. |
| 7,166,816 B1 | 1/2007 | Chen et al. |
| 7,179,255 B2 | 2/2007 | Lettice et al. |
| 7,186,234 B2 | 3/2007 | Dahla et al. |
| 7,189,939 B2 | 3/2007 | Lee et al. |
| 7,189,940 B2 | 3/2007 | Kumar et al. |
| 7,192,428 B2 | 3/2007 | Eggers et al. |
| 7,199,399 B2 | 4/2007 | Chin-Lung et al. |
| 7,201,750 B1 | 4/2007 | Eggers et al. |
| 7,214,280 B2 | 5/2007 | Kumar et al. |
| 7,214,934 B2 | 5/2007 | Stevenson |
| 7,217,268 B2 | 5/2007 | Eggers et al. |
| 7,217,903 B2 | 5/2007 | Bayer et al. |
| 7,220,261 B2 | 5/2007 | Truckai et al. |
| 7,227,097 B2 | 6/2007 | Kumar et al. |
| 7,238,185 B2 | 7/2007 | Palanker et al. |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,271,363 B2 | 9/2007 | Lee et al. |
| 7,275,344 B2 | 10/2007 | Woodmansee, III et al. |
| 7,276,063 B2 | 10/2007 | Davison et al. |
| 7,282,244 B2 | 10/2007 | Schaepkens et al. |
| 7,292,191 B2 | 11/2007 | Anderson |
| 7,297,143 B2 | 11/2007 | Woloszko et al. |
| 7,297,145 B2 | 11/2007 | Woloszko et al. |
| 7,298,091 B2 | 11/2007 | Pickard et al. |
| 7,309,843 B2 | 12/2007 | Kumar et al. |
| 7,311,708 B2 | 12/2007 | McClurken |
| 7,316,682 B2 | 1/2008 | Konesky |
| 7,318,823 B2 | 1/2008 | Sharps et al. |
| 7,331,957 B2 | 2/2008 | Woloszko et al. |
| 7,353,771 B2 | 4/2008 | Millner et al. |
| 7,355,379 B2 | 4/2008 | Kitamura et al. |
| 7,357,798 B2 | 4/2008 | Sharps et al. |
| 7,361,175 B2 | 4/2008 | Suslov |
| 7,382,129 B2 | 6/2008 | Mills |
| 7,387,625 B2 | 6/2008 | Hovda et al. |
| 7,393,351 B2 | 7/2008 | Woloszko et al. |
| 7,399,944 B2 | 7/2008 | DeVries et al. |
| 7,410,669 B2 | 8/2008 | Dieckhoff et al. |
| 7,419,488 B2 | 9/2008 | Ciarrocca et al. |
| 7,426,900 B2 | 9/2008 | Brcka |
| 7,429,260 B2 | 9/2008 | Underwood et al. |
| 7,429,262 B2 | 9/2008 | Woloszko et al. |
| 7,431,857 B2 | 10/2008 | Shannon et al. |
| 7,435,247 B2 | 10/2008 | Woloszko et al. |
| 7,442,191 B2 | 10/2008 | Hovda et al. |
| 7,445,619 B2 | 11/2008 | Auge, II et al. |
| 7,449,021 B2 | 11/2008 | Underwood et al. |
| 7,453,403 B2 | 11/2008 | Anderson |
| 7,458,973 B2 | 12/2008 | Ouchi |
| 7,459,899 B2 | 12/2008 | Mattaboni et al. |
| 7,468,059 B2 | 12/2008 | Eggers et al. |
| 7,480,299 B2 | 1/2009 | O'Keeffe et al. |
| 7,489,206 B2 | 2/2009 | Kotani et al. |
| 7,491,200 B2 | 2/2009 | Underwood |
| 7,497,119 B2 | 3/2009 | Brooks et al. |
| 7,498,000 B2 | 3/2009 | Pekshev et al. |
| 7,506,014 B2 | 3/2009 | Drummond |
| 7,507,236 B2 | 3/2009 | Eggers et al. |
| 7,510,665 B2 | 3/2009 | Shannon et al. |
| 7,511,246 B2 | 3/2009 | Morrisroe |
| 7,549,990 B2 | 6/2009 | Canady |
| 7,563,261 B2 | 7/2009 | Carmel et al. |
| 7,566,333 B2 | 7/2009 | Van Wyk et al. |
| 7,572,255 B2 | 8/2009 | Sartor et al. |
| 7,578,817 B2 | 8/2009 | Canady |
| 7,578,818 B2 | 8/2009 | Platt |
| 7,589,473 B2 | 9/2009 | Suslov |
| 7,601,150 B2 | 10/2009 | Farin |
| 7,608,839 B2 | 10/2009 | Coulombe et al. |
| 7,611,509 B2 | 11/2009 | Van Wyk |
| 7,628,787 B2 | 12/2009 | Sartor et al. |
| 7,632,267 B2 | 12/2009 | Dahla |
| 7,633,231 B2 | 12/2009 | Watson |
| 7,648,503 B2 | 1/2010 | Podhajsky |
| 7,666,478 B2 | 2/2010 | Paulussen et al. |
| 7,691,101 B2 | 4/2010 | Davison et al. |
| 7,691,102 B2 | 4/2010 | Podhajsky et al. |
| 7,708,733 B2 | 5/2010 | Sanders et al. |
| 7,715,889 B2 | 5/2010 | Ito |
| 7,758,575 B2 | 7/2010 | Beller |
| 7,824,398 B2 | 11/2010 | Woloszko et al. |
| 7,879,034 B2 | 2/2011 | Woloszko et al. |
| 7,887,891 B2 | 2/2011 | Rius |
| 7,892,223 B2 | 2/2011 | Geiselhart |
| 7,892,230 B2 | 2/2011 | Woloszko |
| 7,901,403 B2 | 3/2011 | Woloszko et al. |
| 7,940,008 B2 | 5/2011 | Mattaboni et al. |
| 7,949,407 B2 | 5/2011 | Kaplan et al. |
| 8,994,270 B2 | 3/2015 | Koo et al. |
| 2001/0025177 A1 | 9/2001 | Woloszko et al. |
| 2001/0054601 A1 | 12/2001 | Ding |
| 2002/0014832 A1 | 2/2002 | Moradi et al. |
| 2002/0022836 A1 | 2/2002 | Goble et al. |
| 2002/0022838 A1 | 2/2002 | Cunningham et al. |
| 2002/0023899 A1 | 2/2002 | Khater et al. |
| 2002/0092826 A1 | 7/2002 | Ding |
| 2002/0125207 A1 | 9/2002 | Ono et al. |
| 2002/0132380 A1 | 9/2002 | Nakano et al. |
| 2003/0006019 A1 | 1/2003 | Johnson et al. |
| 2003/0008327 A1 | 1/2003 | Ornatskaia |
| 2003/0027186 A1 | 2/2003 | Pierce |
| 2003/0036753 A1 | 2/2003 | Morgan et al. |
| 2003/0038912 A1 | 2/2003 | Broer et al. |
| 2003/0075522 A1 | 4/2003 | Weichart et al. |
| 2003/0093073 A1 | 5/2003 | Platt |
| 2003/0097129 A1* | 5/2003 | Davison ............... A61B 18/14 606/41 |
| 2003/0105456 A1 | 6/2003 | Lin |
| 2003/0125727 A1 | 7/2003 | Truckai et al. |
| 2003/0132198 A1 | 7/2003 | Ono et al. |
| 2003/0158545 A1 | 8/2003 | Hovda et al. |
| 2003/0208194 A1 | 11/2003 | Hovda et al. |
| 2004/0007985 A1 | 1/2004 | de Vries et al. |
| 2004/0022669 A1 | 2/2004 | Ruan et al. |
| 2004/0027127 A1 | 2/2004 | Mills |
| 2004/0075375 A1 | 4/2004 | Miyashita et al. |
| 2004/0086434 A1 | 5/2004 | Gadgil et al. |
| 2004/0111219 A1 | 6/2004 | Gulati |
| 2004/0116918 A1 | 6/2004 | Konesky |
| 2004/0129212 A1 | 7/2004 | Gadgil et al. |
| 2004/0138658 A1 | 7/2004 | Farin et al. |
| 2004/0140194 A1 | 7/2004 | Taylor et al. |
| 2004/0181220 A1 | 9/2004 | Farin |
| 2005/0015001 A1 | 1/2005 | Lec et al. |
| 2005/0017646 A1 | 1/2005 | Boulos et al. |
| 2005/0080413 A1 | 4/2005 | Canady |
| 2005/0103748 A1 | 5/2005 | Yamaguchi et al. |
| 2005/0107786 A1 | 5/2005 | Canady |
| 2005/0118350 A1 | 6/2005 | Koulik et al. |
| 2005/0149012 A1 | 7/2005 | Penny et al. |
| 2005/0153159 A1 | 7/2005 | Sugiyama et al. |
| 2005/0205212 A1 | 9/2005 | Singh et al. |
| 2005/0234439 A1 | 10/2005 | Underwood |
| 2005/0288665 A1 | 12/2005 | Woloszko |
| 2006/0004354 A1 | 1/2006 | Suslov |
| 2006/0011465 A1 | 1/2006 | Burke et al. |
| 2006/0017388 A1 | 1/2006 | Stevenson |
| 2006/0036239 A1 | 2/2006 | Canady |

(56) References Cited

U.S. PATENT DOCUMENTS

| | | |
|---|---|---|
| 2006/0038992 A1 | 2/2006 | Morrisroe |
| 2006/0052771 A1 | 3/2006 | Sartor et al. |
| 2006/0065628 A1 | 3/2006 | Vahedi et al. |
| 2006/0084154 A1 | 4/2006 | Jones et al. |
| 2006/0091109 A1 | 5/2006 | Partlo et al. |
| 2006/0127879 A1 | 6/2006 | Fuccione |
| 2006/0172429 A1 | 8/2006 | Nilsson et al. |
| 2006/0175015 A1 | 8/2006 | Chen et al. |
| 2006/0200122 A1 | 9/2006 | Sartor et al. |
| 2006/0224146 A1 | 10/2006 | Lin |
| 2006/0253117 A1 | 11/2006 | Hovda et al. |
| 2006/0266735 A1 | 11/2006 | Shannon et al. |
| 2006/0278254 A1 | 12/2006 | Jackson |
| 2007/0014752 A1 | 1/2007 | Roy et al. |
| 2007/0021747 A1 | 1/2007 | Suslov |
| 2007/0021748 A1 | 1/2007 | Suslov |
| 2007/0027440 A1 | 2/2007 | Altshuler et al. |
| 2007/0029292 A1 | 2/2007 | Suslov et al. |
| 2007/0029500 A1 | 2/2007 | Coulombe et al. |
| 2007/0039389 A1 | 2/2007 | Brooks et al. |
| 2007/0045561 A1 | 3/2007 | Cooper |
| 2007/0068899 A1 | 3/2007 | Yoon |
| 2007/0084563 A1 | 4/2007 | Holland |
| 2007/0087455 A1 | 4/2007 | Hoffman |
| 2007/0106288 A1 | 5/2007 | Woloszko et al. |
| 2007/0149970 A1 | 6/2007 | Schnitzler et al. |
| 2007/0210035 A1 | 9/2007 | Twarog et al. |
| 2007/0213704 A1 | 9/2007 | Truckai et al. |
| 2007/0251920 A1 | 11/2007 | Hoffman |
| 2007/0255271 A1 | 11/2007 | Dabney et al. |
| 2007/0258329 A1 | 11/2007 | Winey |
| 2007/0282322 A1 | 12/2007 | Dabney et al. |
| 2007/0292972 A1 | 12/2007 | Paulussen et al. |
| 2008/0023443 A1 | 1/2008 | Paterson et al. |
| 2008/0039832 A1 | 2/2008 | Palanker et al. |
| 2008/0050291 A1 | 2/2008 | Nagasawa |
| 2008/0083701 A1 | 4/2008 | Shao et al. |
| 2008/0099434 A1 | 5/2008 | Chandrachood et al. |
| 2008/0099435 A1 | 5/2008 | Grimbergen |
| 2008/0099436 A1 | 5/2008 | Grimbergen |
| 2008/0108985 A1 | 5/2008 | Konesky |
| 2008/0122252 A1 | 5/2008 | Corke et al. |
| 2008/0122368 A1 | 5/2008 | Saito et al. |
| 2008/0125772 A1 | 5/2008 | Stone et al. |
| 2008/0167398 A1 | 7/2008 | Patil et al. |
| 2008/0179290 A1 | 7/2008 | Collins et al. |
| 2008/0185366 A1 | 8/2008 | Suslov |
| 2008/0268172 A1 | 10/2008 | Fukuda et al. |
| 2008/0284506 A1 | 11/2008 | Messer |
| 2008/0292497 A1 | 11/2008 | Vangeneugden et al. |
| 2009/0039789 A1 | 2/2009 | Nikolay |
| 2009/0048594 A1 | 2/2009 | Sartor et al. |
| 2009/0054893 A1 | 2/2009 | Sartor et al. |
| 2009/0054896 A1 | 2/2009 | Fridman et al. |
| 2009/0064933 A1 | 3/2009 | Liu et al. |
| 2009/0076505 A1 | 3/2009 | Arts |
| 2009/0216226 A1 | 8/2009 | Davison et al. |
| 2009/0275941 A1 | 11/2009 | Sartor et al. |
| 2010/0016856 A1 | 1/2010 | Platt, Jr. |
| 2010/0042094 A1 | 2/2010 | Arts |
| 2010/0069902 A1 | 3/2010 | Sartor et al. |
| 2010/0089742 A1 | 4/2010 | Suslov |
| 2010/0114096 A1 | 5/2010 | Podhajsky |
| 2010/0125267 A1 | 5/2010 | Lee et al. |
| 2010/0130973 A1 | 5/2010 | Choi et al. |
| 2010/0204690 A1 | 8/2010 | Bigley et al. |
| 2011/0101862 A1 | 5/2011 | Koo et al. |
| 2011/0139751 A1 | 6/2011 | Koo et al. |
| 2012/0029506 A1 | 2/2012 | Johnson |
| 2013/0053762 A1* | 2/2013 | Rontal ............... A61B 1/0051 604/24 |

FOREIGN PATENT DOCUMENTS

| | | |
|---|---|---|
| DE | 4139029 A1 | 6/1993 |
| DE | 4326037 A1 | 2/1995 |
| DE | 9117019 U1 | 3/1995 |
| DE | 19524645 A1 | 2/1997 |
| DE | 19537897 A1 | 3/1997 |
| DE | 9117299 U1 | 3/2000 |
| DE | 19848784 A1 | 5/2000 |
| DE | 29724247 U1 | 8/2000 |
| EP | 0016542 A2 | 10/1980 |
| EP | 0366876 A1 | 5/1990 |
| EP | 0495699 A1 | 7/1992 |
| EP | 0602764 A1 | 6/1994 |
| EP | 0956827 A1 | 11/1999 |
| EP | 1174901 A2 | 1/2002 |
| EP | 1978038 A1 | 10/2008 |
| FR | 1340509 A | 10/1963 |
| JP | 61-159953 A | 7/1986 |
| JP | 62-130777 | 6/1987 |
| JP | 03-149797 | 6/1991 |
| JP | H06-119995 A | 4/1994 |
| JP | 8-243755 | 9/1996 |
| JP | 2000-286094 A | 10/2000 |
| JP | 2000286094 A | 10/2000 |
| JP | 2001-501485 A | 2/2001 |
| JP | 2001332399 A | 11/2001 |
| JP | 2003007497 A | 1/2003 |
| JP | 2003049276 A | 2/2003 |
| JP | 2003093869 A | 4/2003 |
| JP | 2005-522824 A | 7/2005 |
| JP | 2005-526904 A | 9/2005 |
| JP | 2005-528737 A | 9/2005 |
| JP | 2005276618 A | 10/2005 |
| JP | 2006114450 A | 4/2006 |
| JP | 2006310101 A | 11/2006 |
| JP | 2007188748 A | 7/2007 |
| JP | 2007207540 A | 8/2007 |
| JP | 2008041495 A | 2/2008 |
| JP | 2008071656 A | 3/2008 |
| JP | 2010-242857 A | 10/2010 |
| SU | 1438745 A1 | 11/1988 |
| WO | 9901887 A1 | 1/1999 |
| WO | 9936940 A2 | 7/1999 |
| WO | 0139555 A1 | 5/2001 |
| WO | 03/085693 A1 | 10/2003 |
| WO | 2004032176 A1 | 4/2004 |
| WO | 2004094306 A1 | 11/2004 |
| WO | 2006116252 A2 | 11/2006 |
| WO | 2009/080273 A1 | 7/2009 |
| WO | 2009/146432 A1 | 12/2009 |
| WO | 2009146439 A1 | 12/2009 |
| WO | 2010008062 A1 | 1/2010 |
| WO | 2010146438 A1 | 12/2010 |
| WO | 2011123125 A1 | 10/2011 |
| WO | 2012153332 A2 | 11/2012 |

OTHER PUBLICATIONS

Extended European Search Report from Application No. EP 14154299.3 dated Jun. 18, 2014.

European Communication and Search Report, corresponding to European Application No. 14154624.2, dated Oct. 28, 2015; 9 total pages.

Park et al., "Atmospheric-pressure plasma sources for biomedical applications", Plasma sources Science and Technology, vol. 21, No. 4, Invited Review, Jun. 2012; 21 pages.

Japanese Office Action (with English translation), dated Nov. 17, 2015, corresponding to Japanese Application No. 2015-009663; 8 total pages.

European Search Report dated Dec. 9, 2014, corresponding to European Application No. 09 84 5329; 8 pages.

Y. Ushio, et al., "General Film Behaviour 299 Secondary Electron Emission Studies on Mg0 Films," Thin Solid Films, Jan. 1, 1988; pp. 299-308.

Ward et al., "A Significant New Contribution to Radical Head and Neck Surgery"; Arch Otolaryngology, Head and Neck Surg., vol. 115 pp. 921-923 (Aug. 1989).

(56) References Cited

OTHER PUBLICATIONS

Lieberman et al., "Capacitive Discharges", Principles of Plasma Discharges and Materials Processing, John Wiley & Son, Inc. (2005) pp. 387-460.
Moore et al., "Confined Geometry Interactions of Downstream RF-Excited Atmospheric Plasma Wires", IEEE Transactions on Plasma Science, 0093-3813, (2008) pp. 1-2.
Walsh et al., "Contrasting Characteristics of Pulsed and Sinusoidal Cold Atmospheric Plasma Jets", Applied Physics Letters, 88, 171501 (2006) pp. 1-3.
Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.
Xu et al., "DBD Plasma Jet in Atmospheric Pressure Argon", IEEE Transactions on Plasma Science, vol. 36, No. 4, (Aug. 2008), pp. 1352-1353.
Alfred Grill, "Electron Cyclotron Resonance Plasmas", Cold Plasma in Materials Fabrication, IEEE Press (1994) pp. 40-43.
Brand et al., "Electrosurgical Debulking of Ovarian Cancer: A New Technique Using the Argon Beam Coagulator"; Gynecologic Oncology 39 pp. 115-118 (1990).
Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Brian Chapman, "Matching Networks", Glow Discharge Processes, John Wiley & Sons Inc., NY, (1980) pp. 153-172.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. A Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for in Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).
Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
Sobolewski, Mark A., "Current and Voltage Measurements in the Gaseous Electronics Conference RF Reference Cell". J. Res. Natl. Inst. Stand. Technol. 100, 341; Apr. 1995.
Hernandez et al., "A Controlled Study of the Argon Beam Coagultor for Partial Nephrectomy"; The Journal of Urology, vol. 143, May (1990) J. Urol. 143: pp. 1062-1065.
U.S. Appl. No. 08/383,162, filed Feb. 3, 1995, Lawrence K. Pacer.
U.S. Appl. No. 08/619,380, filed Mar. 21, 1996, Gene H. Arts.
U.S. Appl. No. 08/621,151, filed Mar. 21, 1996, Robert B. Stoddard.
U.S. Appl. No. 08/878,694, filed Jun. 19, 1997, Lawrence K Pacer.
U.S. Appl. No. 09/270,856, filed Mar. 17, 1999, Gene H. Arts.
U.S. Appl. No. 09/504,640, filed Feb. 16, 2000, James Steven Cunningham.
U.S. Appl. No. 09/666,312, filed Sep. 21, 2000, Robert C. Platt.
U.S. Appl. No. 14/085,339, filed Nov. 20, 2013, Friedrichs et al.
U.S. Appl. No. 14/155,636, filed Jan. 15, 2014, Koo.
U.S. Appl. No. 14/157,254, filed Jan. 16, 2014, Koo.
U.S. Appl. No. 14/159,758, filed Jan. 21, 2014, Sartor.
U.S. Appl. No. 14/164,785, filed Jan. 27, 2014, Collins.
Japanese Notice of Final Rejection and Denial of Entry of Amendment (with English translation), issued Apr. 2, 2015, corresponding to Japanese Patent Application No. 2012-513022; 10 total pages.
Extended European Search Report corresponding to European Application No. 09755793.8, dated Jul. 21, 2014; 8 pages.
Extended European Search Report issued in Appl. No. 10849146.5 dated Sep. 26, 2013; 6 pages.
Japanese Notice of Final Rejection and Denial of Entry of Amendment (with English translation), dated Jun. 2, 2015, corresponding to Japanese Patent Application No. 2013-502548; 15 total pages.
English translation of Japanese Notice of Reasons for Rejection, dated Feb. 18, 2014, corresponding to Japanese Patent Application No. 2013-502548; 6 pages.
English translation of Japanese Notice of Reasons for Rejection, dated Oct. 7, 2014, corresponding to Japanese Patent Application No. 2013-502548; 6 pages.
Australian Patent Examination Report No. 1, dated Apr. 17, 2014, corresponding to Australian Patent Application No. 2010349784; 3 pages.
European Communication dated Jun. 17, 2014, corresponding to European Patent Application No. 10849146.5; 6 pages.
European Communication/Examination Report dated Jul. 14, 2015, corresponding to European Patent Application No. 09 845 329.3; 8 pages.
European Communication dated Oct. 22, 2015, corresponding to European Patent Application No. 09755793.8; 9 pages.
European Search Report No. 14/158043.1 dated Oct. 28, 2014.

\* cited by examiner

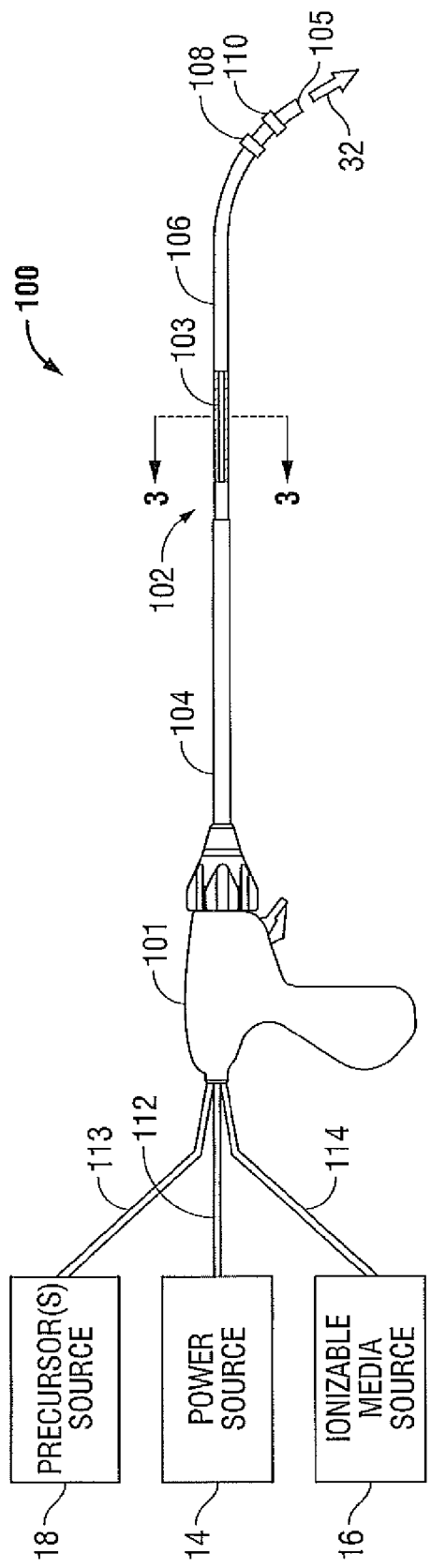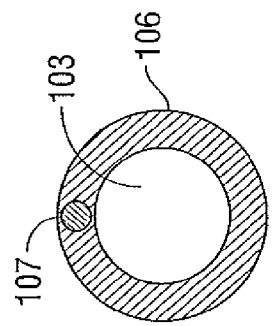
FIG. 2
FIG. 3

SYSTEM AND METHOD FOR SINUS SURGERY

CROSS REFERENCE TO RELATED APPLICATION

The present application claims the benefit of and priority to U.S. Provisional Application Ser. No. 61/773,609, filed on Mar. 6, 2013, the entire contents of which are incorporated herein by reference.

BACKGROUND

Technical Field

The present disclosure relates to plasma devices and processes for surface processing and tissue removal. More particularly, the disclosure relates to a system and method for generating and directing chemically reactive, plasma-generated species in a plasma device along with excited-state species (e.g., energetic photons) that are specific to the supplied feedstocks for treating tissue.

Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

Chronic sinusitis originates from several sources including, but not limited to, infection by bacteria that may form biofilms, fungus that can form large fungal masses within the sinus, allergic reactions to infecting agents, chronic viral conditions such as HPV, and combinations thereof. These sources create inflammation in the sinus cavity that result in eosinophils, which in turn concentrate in the sinuses creating even greater inflammation and the degeneration of the mucosa into polyp formation and weakening of the underlying bone mass. Over time the sinuses cavities fill with foreign material or polyps that originate from the mucosa that lines the sinus cavity. Conventional treatments strip the sinus cavity of all mucosa, which results in the sinus lining reforming from scar tissue rather than epithelial mucosa. More conservative conventional treatments focus on removing the bulk of the material while attempting to preserve as much mucosa as possible. The preferred surgical tool for sinus surgery is a microdebrider available from many manufacturers and well known in the industry. These devises have no tissue selective properties and cut the softened bone equally as well as the overlying tissue using mechanical cutting.

SUMMARY

Plasmas have broad applicability to provide alternative solutions to industrial, scientific and medical needs, especially workpiece surface processing at low temperature. Plasmas may be delivered to a workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Plasmas may also remove a distinct upper layer of a workpiece but have little or no effect on a separate underlayer of the workpiece or it may be used to selectively remove a particular tissue from a mixed tissue region or selectively remove a tissue with minimal effect to adjacent organs of different tissue type.

One suitable application of the unique chemical species is to drive non-equilibrium or selective chemical reactions at or within the workpiece to provide for selective removal of only certain types of materials. Such selective processes are especially sought in biological tissue processing (e.g., mixed or multi-layered tissue), which allows for cutting and removal of tissue at low temperatures with differential selectivity to underlayers and adjacent tissues. This is particularly useful for removal of biofilms, mixtures of fatty and muscle tissue, debridement of surface layers and removing of epoxy and other non-organic materials during implantation procedures.

The plasma species are capable of modifying the chemical nature of tissue surfaces by breaking chemical bonds, substituting or replacing surface-terminating species (e.g., surface functionalization) through volatilization, gasification or dissolution of surface materials (e.g., etching). With proper techniques, material choices and conditions, one can remove one type of tissue entirely without affecting a nearby different type of tissue. Controlling plasma conditions and parameters (including S-parameters, V, I, $\Theta$, and the like) allows for the selection of a set of specific particles, which, in turn, allows for selection of chemical pathways for material removal or modification as well as selectivity of removal of desired tissue type. The present disclosure provides for a system and method for creating plasma under a broad range of conditions including tailored geometries, various plasma feedstock media, number and location of electrodes and electrical excitation parameters (e.g., voltage, current, phase, frequency, pulse condition, etc.).

The supply of electrical energy that ignites and sustains the plasma discharge is delivered through substantially conductive electrodes that are in contact with the ionizable media and other plasma feedstocks. The present disclosure also provides for methods and apparatus that utilize specific electrode structures that improve and enhance desirable aspects of plasma operation such as higher electron temperature and higher secondary emission. In particular, the present disclosure provides for porous media for controlled release of chemical reactants.

Controlling plasma conditions and parameters allows for selection of a set of specific particles, which, in turn, allows for selection of chemical pathways for material removal or modification as well as selectivity of removal of desired tissue type. The present disclosure also provides for a system and method for generating plasmas that operate at or near atmospheric pressure. The plasmas include electrons that drive reactions at material surfaces in concert with other plasma species. Electrons delivered to the material surface can initiate a variety of processes including bond scission, which enables volatilization in subsequent reactions. The electron-driven reactions act synergistically with associated fluxes to achieve removal rates of material greater than either of the reactions acting alone.

A method for treating a sinus cavity is provided by the present disclosure. The method includes the steps of inserting a plasma applicator into a sinus cavity defined in a bone mass, positioning the plasma applicator adjacent a tissue formation, generating a selectively reactive plasma effluent at the plasma applicator and directing the selectively reactive plasma effluent at the tissue formation. The selective nature of the reactive plasma enables treatment of specific targets inside the sinus while minimizing the effect on other tissues. Such treatment includes, but not limited to, sterilization of bacterial colonies, vaporization of unwanted tissues or foreign masses, stimulation of tissues by enriching the content of reactive oxygen and nitrous oxide pathways, and combinations thereof.

A method for treating a tissue cavity is also contemplated by the present disclosure. The method includes the steps of inserting a plasma applicator into a tissue cavity and positioning a plasma applicator adjacent the tissue formation. The plasma applicator includes a shaft having a proximal portion and a deflectable distal portion and a lumen defined therein terminating in an opening at a distal end of the distal portion. The lumen is in fluid communication with an ionizable media source and one or more electrodes disposed at the distal portion and coupled to a power source. The method also includes the steps of generating a selectively reactive plasma effluent at the plasma applicator and directing the selectively reactive plasma effluent at the tissue formation.

The present disclosure also provides for a method for treating a sinus cavity. The method includes the steps of inserting a plasma applicator into a sinus cavity defined in a bone mass and positioning the plasma applicator adjacent a tissue formation. The method also includes the steps of selecting one or more precursor feedstocks having higher chemical reactivity with the tissue formation than with the bone mass of the sinus cavity, supplying ionizable media and the precursor feedstocks to the plasma applicator and igniting the ionizable media and the precursor feedstocks at the plasma applicator to form a selectively reactive plasma effluent. The method further includes the step of directing the selectively reactive plasma effluent at the tissue formation.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein:

FIG. 2 is a schematic view of a plasma device according to the present disclosure;

FIG. 3 is a cross-sectional view of the plasma device of FIG. 2 along lines 3-3;

DETAILED DESCRIPTION

Plasmas are generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuit that is used to deliver electrical energy to the circuit affects many properties and requirements of the plasma. The performance of the plasma chemical generation, the delivery system and the design of the electrical excitation circuitry are interrelated—as the choices of operating voltage, frequency and current levels (as well as phase) effect the electron temperature and electron density. Further, choices of electrical excitation and plasma device hardware also determine how a given plasma system responds dynamically to the introduction of new ingredients to the host plasma gas or liquid media. The corresponding dynamic adjustment of the electrical drive, such as via dynamic match networks or adjustments to voltage, current, or excitation frequency may be used to maintain controlled power transfer from the electrical circuit to the plasma.

Figure 1:
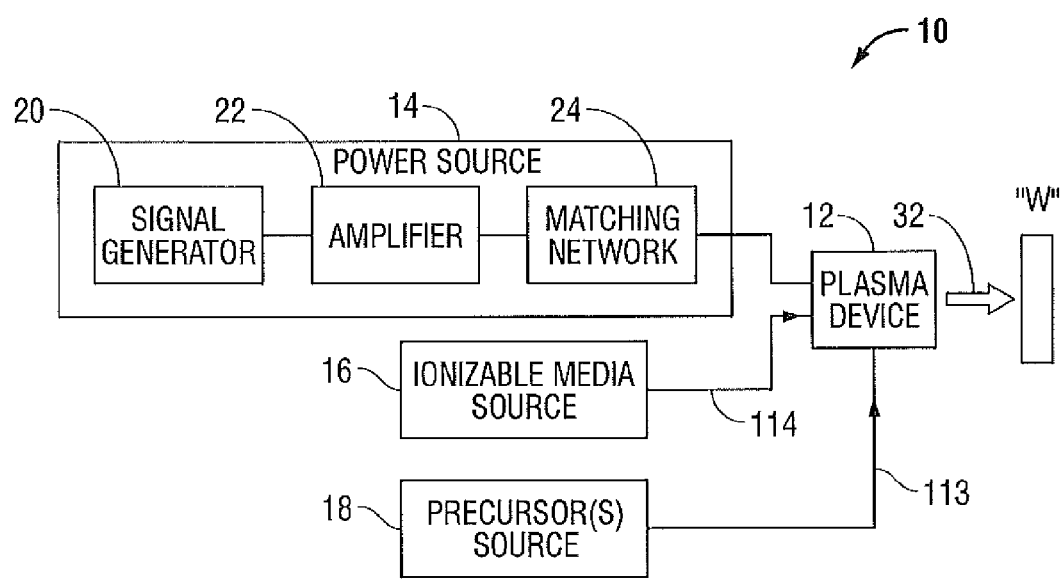
FIG. 1 is a schematic diagram of a plasma system according to the present disclosure.

Referring initially to FIG. 1, a plasma system 10 is disclosed. The system 10 includes a plasma device 12 that is coupled to a power source 14, an ionizable media source 16 and a precursor source 18. Power source 14 includes any suitable components for delivering power or matching impedance to plasma device 12. More particularly, the power source 14 may be any radio frequency generator or other suitable power source capable of producing power to ignite the ionizable media to generate plasma. The plasma device 12 may be utilized as an electrosurgical pencil for application of plasma to tissue and the power source 14 may be an electrosurgical generator that is adapted to supply the device 12 with electrical power at a frequency from about 0.1 MHz to about 2.450 MHz and in another embodiment from about 1 MHz to about 13.56 MHz. The plasma may also be ignited by using continuous or pulsed direct current (DC) electrical energy.

The precursor source 18 may be a bubbler or a nebulizer configured to aerosolize precursor feedstocks prior to introduction thereof into the device 12. The precursor source 18 may also be a micro droplet or injector system capable of generating predetermined refined droplet volume of the precursor feedstock from about 1 femtoliter to about 1 nanoliter in volume. The precursor source 18 may also include a microfluidic device, a piezoelectric pump, or an ultrasonic vaporizer.

The system 10 provides a flow of plasma through the device 12 to a workpiece "W" (e.g., tissue). Plasma feedstocks, which include ionizable media and precursor feedstocks, are supplied by the ionizable media source 16 and the precursor source 18, respectively, to the plasma device 12. During operation, the precursor feedstock and the ionizable media are provided to the plasma device 12 where the plasma feedstocks are ignited to form plasma effluent containing ions, radicals, photons from the specific excited species and metastables that carry internal energy to drive desired chemical reactions in the workpiece "W" (e.g., tissue) or at the surface thereof. The feedstocks may be mixed upstream from the ignition point or midstream thereof (e.g., at the ignition point) of the plasma effluent, as shown in FIG. 1 and described in more detail below.

The ionizable media source 16 provides ionizable feedstock to the plasma device 12. The ionizable media source 16 is coupled to the plasma device 12 and may include a storage tank, a pump, and a cooling source (not explicitly shown). The ionizable media may be a liquid or a gas such as argon, helium, neon, krypton, xenon, radon, carbon dioxide, nitrogen, hydrogen, oxygen, etc. and their mixtures, and the like, or a liquid. These and other gases may be initially in a liquid form that is gasified during application. The gases maybe cooled prior to ionization such as energy is added the ionization process the effluent remains below the targeted maximum temperature associated with cold plasma reactions.

The precursor source 18 provides precursor feedstock to the plasma device 12. The precursor feedstock may be either in solid, gaseous or liquid form and may be mixed with the ionizable media in any state, such as solid, liquid (e.g., particulates or droplets), gas, and the combination thereof. The precursor source 18 may include a heater, such that if the precursor feedstock is liquid, it may be heated into gaseous state prior to mixing with the ionizable media.

In one embodiment, the precursors may be any chemical species capable of forming reactive species such as ions, electrons, excited-state (e.g., metastable) species, molecular fragments (e.g., radicals) and the like, when ignited by electrical energy from the power source 14 or when undergoing collisions with particles (electrons, photons, or other energy-bearing species of limited and selective chemical reactivity) formed from ionizable media 16. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the chemical precursors may be water, halogenoalkanes, such as dichloromethane, trichloromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalises such as NaOH, KOH, amines, alkyls, alkenes, and the like. Such chemical precursors may be applied in substantially pure, mixed, or soluble form.

The precursors and their functional groups may be delivered to a surface to react with the surface species (e.g., molecules) of the workpiece "W." In other words, the functional groups may be used to modify or replace existing surface terminations of the workpiece "W." The functional groups react readily with the surface species due to their high reactivity and the reactivity imparted thereto by the plasma. In addition, the functional groups are also reacted within the plasma volume prior to delivering the plasma volume to the workpiece.

Some functional groups generated in the plasma can be reacted in situ to synthesize materials that subsequently form a deposition upon the surface. This deposition may be used for stimulating healing, killing bacteria, and increasing hydrophilic or hydroscopic properties. In addition, deposition of certain function groups may also allow for encapsulation of the surface to achieve predetermined gas/liquid diffusion, e.g., allowing gas permeation but preventing liquid exchange, to bond or stimulate bonding of surfaces, or as a physically protective layer.

With reference to FIGS. 1 and 2, the precursor source 18 and the ionizable media source 16 may be coupled to the plasma device 12 via tubing 114 and 113, respectively. The tubing 114 and 113 may be combined into unified tubing to deliver a mixture of the ionizable media and the precursor feedstock to the device 12 at a proximal end thereof. This allows for the plasma feedstocks, e.g., the precursor feedstock and the ionizable gas, to be delivered to the plasma device 12 simultaneously prior to ignition of the mixture therein.

In another embodiment, the ionizable media source 16 and the precursors source 18 may be coupled to the plasma device 12 via the tubing 114 and 113 at separate connections, such that the mixing of the feedstocks occurs within the plasma device 12 upstream from the ignition point. In other words, the plasma feedstocks are mixed proximally of the ignition point, which may be any point between the respective sources 16 and 18 and the plasma device 12, prior to ignition of the plasma feedstocks to create the desired mix of the plasma effluent species for each specific surface treatment on the workpiece "W."

In a further embodiment, the plasma feedstocks may be mixed midstream, e.g., at the ignition point or downstream of the plasma effluent, directly into the plasma. It is also envisioned that the ionizable media may be supplied to the device 12 proximally of the ignition point, while the precursor feedstocks are mixed therewith at the ignition point. In a further illustrative embodiment, the ionizable media may be ignited in an unmixed state and the precursors may be mixed directly into the ignited plasma. Prior to mixing, the plasma feedstocks may be ignited individually. The plasma feedstock is supplied at a predetermined pressure to create a flow of the medium through the device 12, which aids in the reaction of the plasma feedstocks and produces a plasma effluent. The plasma according to the present disclosure is generated at or near atmospheric pressure under normal atmospheric conditions.

The system 10 also includes a coolant system 15 for cooling the device 12 and particularly the plasma plume 32. The coolant system 15 includes a supply pump 17 and a supply tank 18. The supply pump 17 may be a peristaltic pump or any other suitable type of pump known in the art. The supply tank 17 stores the coolant fluid (e.g., saline, propylene glycol) and, in one embodiment, may maintain the fluid at a predetermined temperature. In another embodiment, the coolant fluid may be a gas and/or a mixture of fluid and gas. The system 10 further includes a negative pressure source 19 to siphon tissue and unreacted components from the treatment site. The negative-pressure source 17 may be a vacuum pump, fan, circulator, and the like and is coupled to the device 12.

With reference to FIGS. 2 and 3, the device 12 is shown as a plasma applicator 100. The applicator 100 includes a handle 101 and a longitudinal shaft 102 coupled thereto. The shaft 102 includes a proximal portion 104 coupled to the handle 101 and a distal portion 106. The catheter shaft 102 includes a plasma lumen 103 defined therein and extending the entire length thereof and terminating in an opening 105 at distal end of the distal portion 106. The shaft 102 may have a diameter from about 5 mm to about 10 mm allowing the applicator 100 to be inserted through operating ports for application of the plasma effluent 32 at the operating site during laparscopic procedures or through natural body orifices. In another embodiment, the applicator 100 may be configured for use within or accompanied by a flexible endoscope.

In one embodiment, the distal portion 106 is configured for controlled deflection. A pull-wire 107 (FIG. 3) or another suitable actuation mechanism extends from the handle 101 at the proximal end of the catheter 100 through a lumen in the catheter shaft 102 and is fastened to the distal portion 106. The pull-wire 107 is movable from a first generally relaxed position wherein the distal portion 106 is disposed in a generally longitudinally-aligned position relative to the proximal portion 104 to a second retracted or tensed position wherein the distal portion 106 flexes (e.g., deflects) from the proximal portion 104 at a desired angle as shown in FIG. 2.

The distal portion 106 is constructed to be more flexible than the proximal portion 104, such that when the handle 101 is pulled back or otherwise actuated, the pull-wire bends the distal portion 106 from an undeflected position to a deflected position. In particular, the proximal portion 104 may include a wire or other support materials (not shown) therein to provide tensile strength to the catheter shaft 102 while still maintaining flexibility for maneuvering through a vascular system. The distal portion 106 is formed from a flexible biocompatible material such as polytetrafluoroethylene, polyurethane, polyimide, and the like to allow for maneuverability thereof.

The applicator 100 includes two or more electrodes 108 and 110 disposed at the distal portion 106. The electrodes 108 and 110 may be formed from a conductive material and have a ring-like shape. The electrodes 108 and 110 may be disposed over the distal portion 106 to provide for capacitive coupling with the ionizable media. In another embodiment, the electrodes 108 and 110 may be formed as needle electrodes (e.g., pointed tip) and may be disposed within the distal portion 106.

The electrodes 108 and 110 are coupled to conductors (not shown) that extend through the catheter shaft 102 and are connected to the power source 14 via electrical connectors 112. The catheter shaft 102 is also coupled to the ionizable media source 16 via gas tubing 114 and to the precursors source 16 via tubing 113. The ionizable media source 16 and the precursors source 16 may include various flow sensors and controllers (e.g., valves, mass flow controllers, etc.) to control the flow of ionizable media to the applicator 100. In particular, the lumen 103 is in gaseous and/or liquid communication with the ionizable media source 16 and the precursors source 18 allowing for the flow of ionizable media and precursor feedstocks to flow through the catheter shaft 102 to the distal portion 106. The ionizable media in conjunction with the precursor feedstocks is ignited by application of energy through the electrodes 108 and 110 to form plasma plume 32 exiting through the opening 105.

The applicator 100 also includes a suction lumen 150 coupled to the negative pressure source 19. This allows for the removal of unreacted feedstocks, debris and tissue particles to be removed from the tissue site. The lumen 150 may be incorporated into the shaft 102 (FIG. 3) or may be a separate tube coupled in parallel to the shaft 102.

The applicator 100 is suitable for treatment of various sinus cavities, such as paranasal sinuses. Sinuses are commonly accessed through nasal passages using open or endoscopic instruments. Treatment of sinus cavities may involve debulking of the soft tissue located within the sinuses to prevent infections thereof. In particular, the goal of the procedure may be to remove polyps, tumors, fungal masses and other tissue structures while preserving as much of the mucosal lining as possible.

Figure 4:
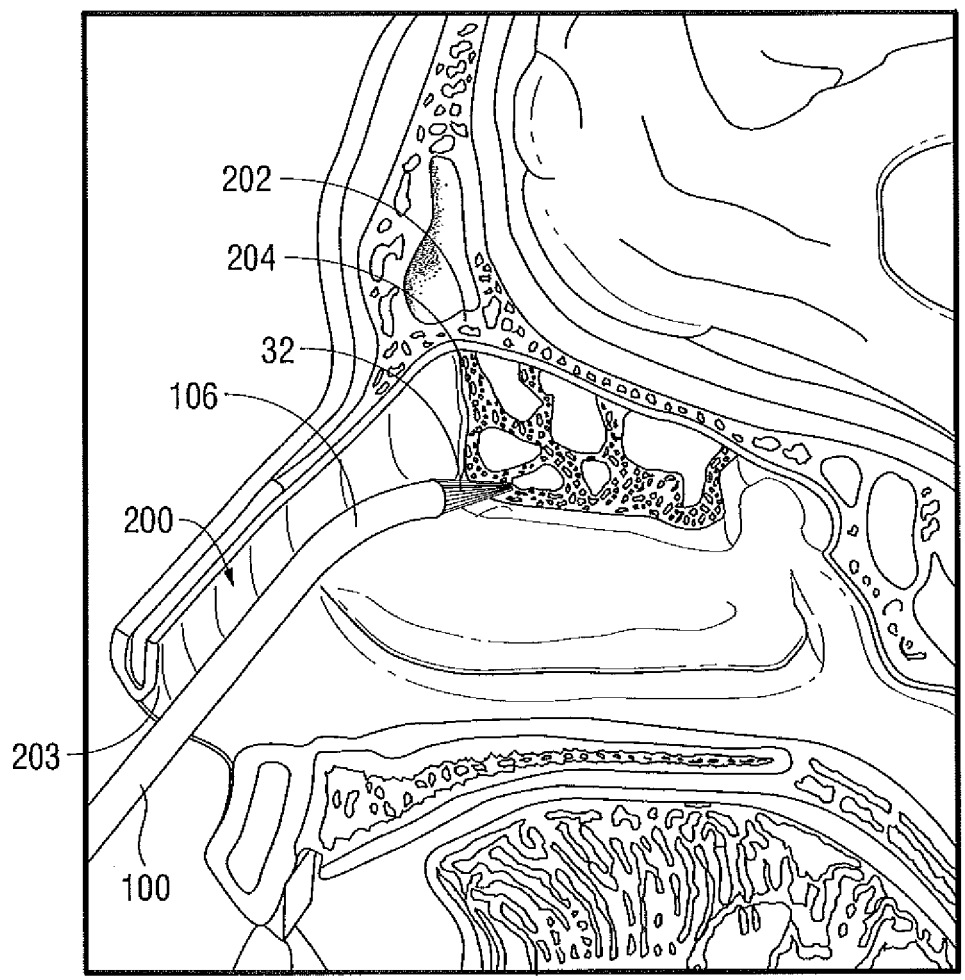
FIG. 4 is an internal perspective view of a surgical site.
Figure 5:
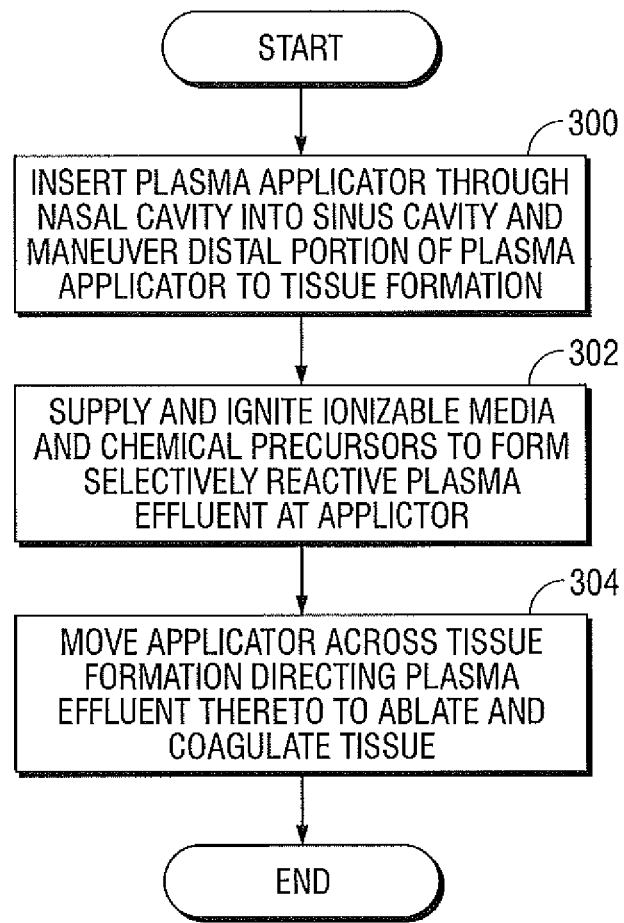
FIG. 5 is a flow chart of a method according to the present disclosure.

With reference to FIGS. 4 and 5, a functional sinus procedure using the applicator 100 is discussed. FIG. 4 illustrates the paranasal sinuses and FIG. 5 illustrates a flow chart of a method for treating the sinuses. The surgical site includes multiple sinus cavities 200 formed within the bone mass 202. The sinus cavity 200 includes a formation 204 (e.g., tumors, polyps, fungal masses, etc.) that affects the health of the sinus cavities 200.

In step 300, the applicator 100 inserted into the sinus cavity 200 through a nasal cavity 203. Access may be gained through or by enlargement of an existing ostium or creating an opening to the sinus cavity 200 from the nasal cavity 203 or perforation through other organs (e.g., percutaneous).

The distal portion 106 may be deflected to direct the plasma effluent 32 toward the tissue formation 204. In one embodiment, the deflection may be from about 0° to about 45° with respect to a longitudinal axis defined by the shaft 102. In step 302, the ionizable media along with precursors is supplied to the applicator 100 and is ignited therein to form the plasma effluent 32. In one embodiment, the ionizable media may be argon, helium or a mixture thereof and the precursors may be hydrogen peroxide, water, oxygen, nitrogen or mixtures thereof.

In step 304, the applicator 100 is moved across the tissue formation 204 ensuring that the plasma effluent 32 is directed at the tissue to remove the soft tissue. As tissue is ablated, unreacted tissue particles and other debris is removed from the treatment site through the suction lumen 150 via the negative pressure source 19. The temperature of the plasma effluent 32 is from about 60°, allowing the plasma to be used within the confines of the sinus cavity 200 without ablating surrounding critical tissue masses. The relatively low temperature of the plasma effluent 32 does not affect its ability to remove tissue, since the primary effect on tissue is due to the chemical reactivity of the plasma constituents (e.g., ionized plasma feedstocks).

The precursors supplied to the applicator 100 are specifically chosen to generate a selectively reactive plasma effluent 32. In other words, the precursors, when ignited, produce a plasma effluent 32 that interacts with certain types of tissue, namely tissue formation 204, and has little to no effect on the underlying bone tissue. The selected precursor feedstocks have higher chemical reactivity with the tissue formation 204 relative to the chemical reactivity with the calcified tissue (e.g., bone). This allows for the plasma effluent 32 to etch and remove the tissue formation 204 without perforating the bone.

The plasma effluent 32 ablates and coagulates tissue via heat to stop bleeding. The plasma effluent 32 effectively ablates tissue formation 204 while simultaneously cauterizing the tissue preventing bleeding. In one embodiment, bleeding may be also controlled by administration of various drugs (e.g., hemostatic agents) that prevent bleeding within the sinus cavity 200. The drugs may be administered topically to the tissue or through the plasma effluent 32 as chemical precursor feedstocks.

Sinus cavities may be very close to the brain or orbit of the eye, making conventional instruments, such as microdebriders very dangerous due to their aggressive cutting action that may remove the surrounding bone tissue and damage nearby organs. In addition, diseased sinuses have already thinned bones further reducing differentiation between targeted soft tissues and bone tissue, thereby further increasing the possibility of perforation into adjacent critical structures.

The present disclosure prevents such damage without requiring great care and expensive surgical navigational systems (e.g., endoscopes) that are practically required when using conventional microdebriders. The present disclosure provides for a chemically reactive plasma that has higher chemical reactivity with the soft tissue than calcified tissue (e.g., bone) thereby etching the soft tissue while leaving calcified or partially calcified tissue unaffected. This provides for safer removal of tissue masses near critical structures. The reactivity, removal rates and/or selectivity of the plasma effluent may be modified by supplying different chemical precursors to the applicator 100 based on the tissue being treated.

The applicator 100 also provides another advantage over mechanical microdebriders, namely, a deflectable distal portion 106. Mechanical debriders and/or cutters have inflexible shafts which are either straight or curved having fixed radial bends in the instrument shaft. Deflection of the distal portion 106 allows for usage of the applicator 100 at virtually any reach within a general target mass or within the sinuses.

The plasma effluent according to the present disclosure also generates little heat and may be produced at a relatively low temperature (e.g., room temperature). This provides another advantage over conventional methods that utilize electrosurgical instruments. Such instruments generate too much heat that is poorly dissipated within the sinuses, which may damage critical structures.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. In particular, as discussed above this allows the tailoring of the relative populations of plasma species to meet needs for the specific process desired on the workpiece surface or in the volume of the reactive plasma, such adapting the disclosed system and method for use on other body cavities where selective removal of tissue is desired.

What is claimed is:

1. A method for treating a sinus cavity, the method comprising the steps of:
    inserting a plasma applicator into a sinus cavity defined in a bone mass;
    positioning the plasma applicator adjacent a tissue formation;
    generating a selectively reactive plasma effluent at the plasma applicator; and
    directing the selectively reactive plasma effluent at the tissue formation,
    wherein the selectively reactive plasma effluent selectively removes the tissue formation without perforating bone.

2. A method according to claim 1, wherein the positioning step further includes the step of:
    deflecting a distal portion of the plasma applicator to direct the distal portion toward the tissue formation.

3. A method according to claim 1, wherein the generating step further includes the steps of:
    supplying ionizable media and at least one precursor feedstock to the plasma applicator; and
    igniting the ionizable media and the at least one precursor feedstock at the plasma applicator to form the selectively reactive plasma effluent.

4. A method according to claim 3, wherein the generating step further includes the step of:
    selecting the at least one precursor feedstock to have a higher chemical reactivity with the tissue formation than with the bone mass of the sinus cavity.

5. A method according to claim 3, wherein the at least one precursor feedstock is selected from the group consisting of hydrogen peroxide, water, oxygen and nitrogen.

6. A method according to claim 3, wherein the ionizable media is selected from the group consisting of argon and helium.

7. A method according to claim 3, further comprising the step of applying at least one hemostatic agent to the tissue formation.

8. A method according to claim 3, wherein the at least one precursor feedstock comprises at least one hemostatic agent.

9. A method according to claim 1, wherein the plasma effluent has a maximum temperature of about 60° C.

* * * * *